United States Patent
Jacobs

(12) 
(10) Patent No.: US 6,402,677 B1
(45) Date of Patent: Jun. 11, 2002

(54) BRACHYTHERAPY SEED NEEDLE WITH WINDOW

(75) Inventor: Charles Jacobs, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/465,845

(22) Filed: Dec. 17, 1999

(51) Int. Cl.[7] .......................... A61M 36/00; A61N 5/00
(52) U.S. Cl. ........................................................ 600/7
(58) Field of Search ................................ 600/7, 1, 2, 3, 600/4, 5, 6, 8; 604/187

(56) References Cited

U.S. PATENT DOCUMENTS

| | | |
|---|---|---|
| 4,402,308 A | 9/1983 | Scott |
| 4,453,928 A | 6/1984 | Steiger |
| 4,535,773 A | 8/1985 | Yoon |
| 4,588,398 A | 5/1986 | Daugherty et al. |
| 4,627,841 A | 12/1986 | Dorr |
| 4,700,692 A | 10/1987 | Baumgartner |
| 4,763,642 A | 8/1988 | Horowitz |
| 4,869,717 A | 9/1989 | Adair |
| 5,147,282 A | 9/1992 | Kan |
| 5,242,373 A | 9/1993 | Scott et al. |
| 5,312,345 A | 5/1994 | Cole |
| 5,334,159 A | 8/1994 | Turkel |
| 5,470,318 A | 11/1995 | Griffith, III et al. |
| 5,487,739 A | 1/1996 | Aebischer et al. |
| 5,540,662 A | 7/1996 | Nicholson |
| 5,860,909 A | 1/1999 | Mick et al. |
| 5,906,574 A | 5/1999 | Kan |
| 5,911,711 A | 6/1999 | Pelkey |
| 5,928,130 A | 7/1999 | Schmidt |
| 5,938,583 A | 8/1999 | Grimm |
| 5,997,463 A | 12/1999 | Cutrer |
| 6,221,003 B1 * | 4/2001 | Sierocuk et al. ............... 600/7 |

FOREIGN PATENT DOCUMENTS

| | | |
|---|---|---|
| WO | PCT 98/01179 | 1/1998 |
| WO | PCT 99/42149 | 8/1999 |

\* cited by examiner

*Primary Examiner*—Kevin Shaver
*Assistant Examiner*—Brian Szmal
(74) *Attorney, Agent, or Firm*—Kilpatrick Stockton LLP

(57) ABSTRACT

A brachytherapy needle comprises a hollow cannula defining a lumen through which radioactive seeds are delivered. A push stylet is telescopically received within the hollow cannula for advancing the radioactive seeds through the lumen of the cannula. The hollow cannula has a window formed in a side wall through which at least a portion of the lumen can be visualized. In the preferred embodiment the window comprises a slot formed in the side wall of the cannula through which radioactive seeds and intervening spacers can be viewed. Also in the preferred embodiment, a transparent covering, advantageously a sleeve of transparent, heat-shrinkable plastic, is disposed over the slot to prevent tissue from lapsing into the slot during implantation of the seeds.

18 Claims, 4 Drawing Sheets

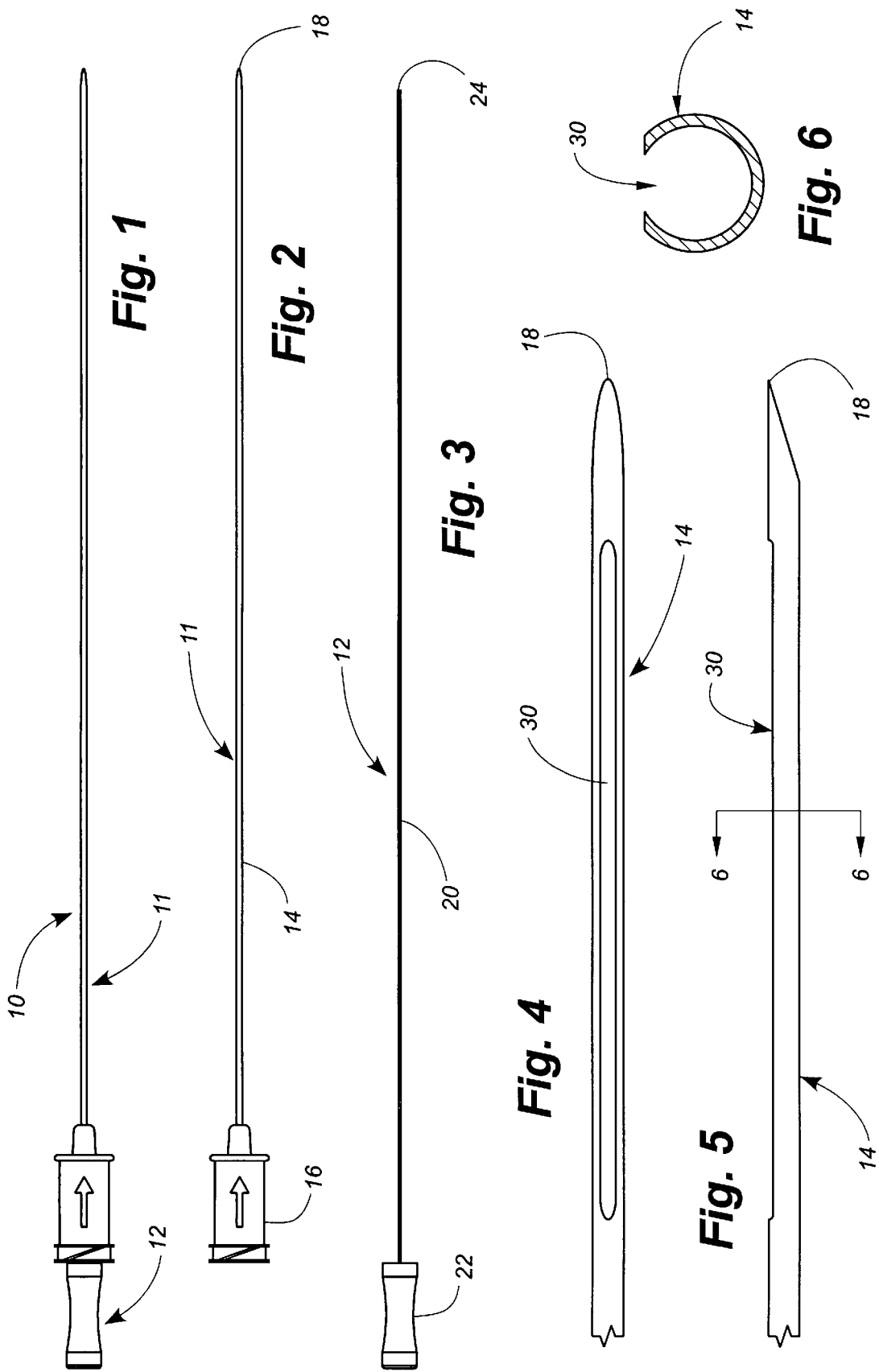

BRACHYTHERAPY SEED NEEDLE WITH WINDOW

TECHNICAL FIELD

The present invention relates generally to surgical instruments and relates more specifically to a needle for implanting brachytherapy seeds within the body of a patient.

BACKGROUND OF THE INVENTION

It is well known to treat tumors with localized radiation by implanting radioactive seeds within the body of the patient within or in the vicinity of the tumor. The seeds typically comprise I-125, Pd-103, or other suitable radioactive agents contained within a pellet or seed to prevent migration of the radioactive material throughout the body of the patient.

Such radioactive seeds, known as "brachytherapy" seeds, are conventionally implanted within the body of the patient by advancing the seeds through a hollow needle. The needle includes a cannula having a leading edge for parting or cutting the patient's tissue so as to dispose the cannula at a position to deploy the seeds with a push rod or stylet. Since it is usually desirable to implant a number of seeds in a single procedure, a plurality of seeds can be loaded into the cannula. To assure proper spacing between adjacent seeds upon implantation, spacers of cat gut or other bioabsorbable material may be placed between adjacent seeds. The stylet is then telescopically positioned into the rearward end of the cannula. This loading procedure is typically performed by a physicist, and the loaded cannula is given to a physician to implant the seeds in the patient. The physician inserts the cannula and stylet into the body of the patient to a location adjacent the tumor. The physician then holds the stylet steady and withdraws the cannula, causing the seeds and spacers to be pushed out into the tissues of the patient as the cannula is retracted.

A problem with this procedure concerns the need to load the seeds and spacers in the proper order. Once the loading procedure has begun, if the physicist is interrupted or becomes distracted, he or she may forget whether the last-loaded element was a seed or a spacer. Since it is not possible for the physicist to see inside the needle, there is no way to verify proper placement of the seeds and spacers without unloading the needle. Failure to load the seeds and spacers in the proper sequence, such as by loading two seeds without an intervening spacer or loading two spacers between adjacent seeds, can result in improper spacing of the seeds within the body of the patient.

Thus, there is a need for a needle for implanting brachytherapy seeds which permits a physician to verify proper loading of seeds and spacers into the needle.

The number and location of brachytherapy seeds used in a given treatment is carefully calculated to deliver a predetermined dose of radiation to the tumor. Since the amount of radiation delivered to a tumor depends upon the spacing and location of the seeds relative to the tumor, optimal brachytherapy treatment requires careful positioning of the seeds. A problem associated with prior art brachytherapy procedures is that friction between the brachytherapy needle and the tissues of the patient can cause the seeds to be improperly positioned. More specifically, as the cannula of the brachytherapy needle is retracted to expose the seeds in the tissues of the patient, friction between the outer surface of the cannula and the patient's tissues causes the tissues to distend. The seeds are deployed into the distended tissue. When the frictional force is removed, the tissue subsequently returns to its normal position, causing the seeds to be displaced as the tissue moves. The seeds may thus not be positioned in the desired locations.

Thus, there is a need for a needle for implanting brachytherapy seeds which minimizes friction between the outer circumference of the brachytherapy needle and the tissues of a patient.

There is a further need for a brachytherapy needle which avoids the problem of deploying seeds into displaced tissue such that the seeds are displaced when the tissue returns to its normal state.

SUMMARY OF THE INVENTION

Stated generally, the present invention relates to a needle for implanting brachytherapy seeds into the body of a patient which addresses the foregoing concerns. In one aspect the device permits a physicist to visually verify proper loading of the seeds and spacers in the needle after the loading process has been completed. In another aspect the device minimizes friction between the outer circumference of the brachytherapy needle and the tissues of a patient so as to avoid the problem of deploying seeds into displaced tissue such that the seeds are displaced when the tissue returns to its normal state. The device operates in a conventional manner and thus does not require the physician to learn how to operate a new device. The device is also inexpensive to manufacture, thus providing advantages over conventional brachytherapy needles without significant increases in manufacturing costs.

Stated somewhat more specifically, the brachytherapy needle of the present invention comprises a hollow cannula defining a lumen through which radioactive seeds and spacers are delivered. A push stylet is telescopically received within the hollow cannula for advancing the radioactive seeds and spacers through the lumen of the cannula. In one aspect the hollow cannula has a window formed in a side wall through which at least a portion of the lumen can be visualized. In the preferred embodiment the window comprises a slot formed in the side wall of the cannula through which radioactive seeds and spacers can be viewed. Also in the preferred embodiment, a transparent covering, advantageously a sleeve of transparent, heat-shrinkable plastic, is disposed over the slot to prevent tissue from lapsing into the slot when the cannula is inserted into the patient's body. In another aspect, a plastic outer sleeve of a lubricious material or having a lubricious coating minimizes friction between the outer surface of the needle and the tissues of the patient. Advantageously a single component functions as both the low-friction sleeve and the transparent window covering.

BRIEF DESCRIPTION OF THE DRAWINGS

FIG. 1 is a top view of a brachytherapy seed needle with window, according to a disclosed embodiment of the present invention.

FIG. 2 is a top view of a hollow cannula of the brachytherapy seed needle of FIG. 1.

FIG. 3 is a side view of a stylet of the brachytherapy seed needle of FIG. 1.

FIG. 4 is a top view of the forward portion of the hollow cannula of FIG. 2.

FIG. 5 is a side view of the cannula portion of FIG. 4.

FIG. 6 is a cross-sectional view taken along line 6—6 of FIG. 5.

DETAILED DESCRIPTION OF THE DISCLOSED EMBODIMENT

Figure 7:
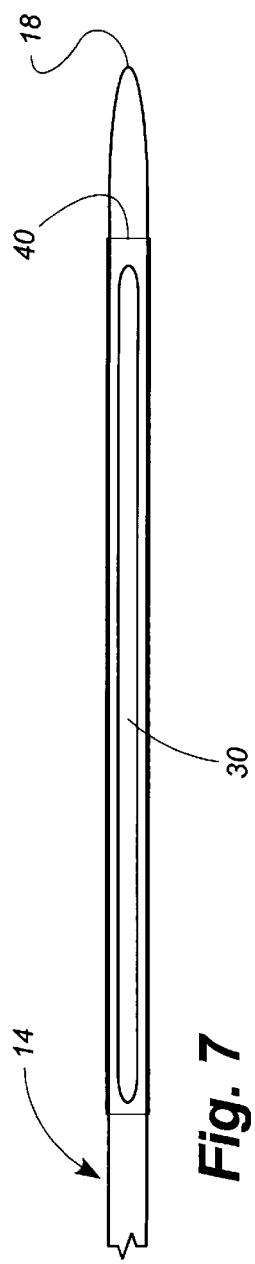
FIG. 7 is a top view of the forward portion of the hollow cannula of FIG. 2 showing a transparent covering positioned over a forward portion of the cannula.

Referring now to the drawings, in which like numerals indicate like elements throughout the several views, FIG. 1 shows a needle 10 comprising a cannula 11 and a stylet 12. As can be seen in FIG. 2, the cannula 11 includes an elongated hollow shaft 14. The shaft 14 is preferably formed from stainless steel but may be formed from any other suitable material, such as a hard plastic, a metal, or a composite material. The cannula 11 further includes a cannula head 16 molded onto the rearward end of the shaft 14. In the disclosed embodiment the cannula 11 has an overall length of approximately 8.76 inches, with the cannula head 16 being approximately 0.885 inches and the exposed length of the cannula shaft 14 being 7.875 inches. The hollow cannula shaft 14 of the disclosed embodiment has an outer diameter of 0.050 inches and an inner diameter of 0.042 inches. The cannula 11 has a beveled cutting edge formed at its forward end 18.

Referring now to FIG. 3, the stylet 12 includes an elongated rod 20 and a stylet head 22 molded onto the rearward end of the rod. The rod 20 is preferably solid and is preferably formed from stainless steel or other art-known material. In the disclosed embodiment the stylet 12 has an overall length of approximately 9.35 inches, with the stylet head 22 being approximately 0.65 inches and the exposed length of the stylet rod 20 being approximately 8.75 inches. The stylet rod 20 has an outer diameter of 0.395 inches. The forward end 24 of the stylet 12 is generally blunt.

With reference again to FIG. 1, the stylet 12 and cannula 11 fit together in coaxial telescoping arrangement, the rod 20 of the stylet residing within the hollow shaft 14 of the cannula. When the stylet 12 and cannula 11 are fitted together in coaxial telescoping arrangement, as shown in FIG. 1, with the forward end of the stylet head 22 butted against the rearward end of the cannula head 16, the forward end 24 of the solid stylet rod 20 terminates just short of the forward end 18 of the cannula shaft 14.

Referring now to FIGS. 4–6, on the top of the cannula shaft 14 adjacent its forward end 18, a slot 30 is formed. In the disclosed embodiment, the slot 30 begins at a point just rearward of the forward end 18 of the cannula shaft 14 and is approximately 4 inches long. The slot 30 of the disclosed embodiment is approximately 0.25 inches in width.

Figure 8:
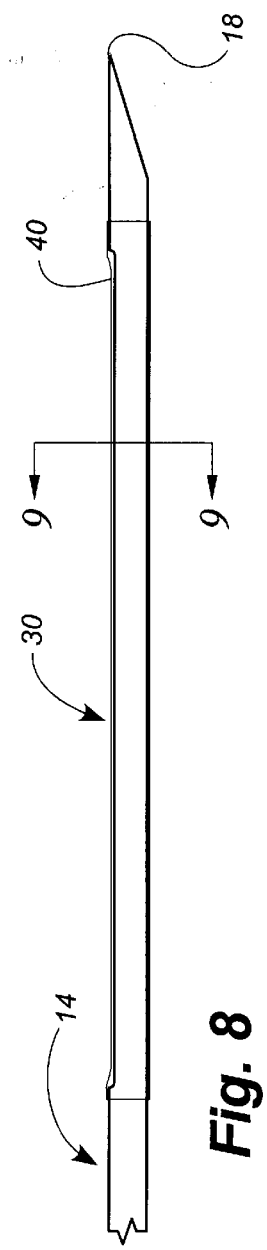
FIG. 8 is a side view of the cannula portion and transparent covering of FIG. 7.
Figure 9:
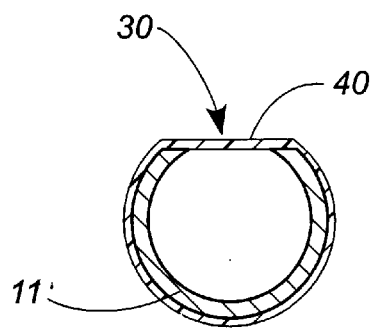
FIG. 9 is a cross-sectional view taken along line 9—9 of FIG. 8.

Referring now to FIGS. 7–9, a transparent sleeve 40 is placed over the outer circumference of a portion of the cannula shaft 14, extending from a location just forward of the forward end of the slot 30 and extending to a location just rearward of the rear end of the slot. The portion of the transparent sleeve 40 which overlies the slot 30 thus forms a window 42 through which the interior of the cannula 11 can be visualized.

In the disclosed embodiment the sleeve 40 is comprised of fluorinated ethylene propylene (FEP) shrink wrap tubing 0.025 inches thick. Tetrafluoroethylene propylene (TFEP) shrink wrap tubing will also produce acceptable results. Both FEP and TFEP shrink wrap tubing are available from various sources, including Zeus Industrial Products, Orangeburg, S.C. To accommodate the outer diameter of the cannula 11 of the disclosed embodiment, a sleeve 40 of FEP shrink wrap having an inner diameter of 0.060 inches is used. When exposed to heat, the sleeve 40 shrinks such that its inner diameter is 0.040 inches. The sleeve 40 is selected such that the recovered inner diameter of the sleeve does not lapse into the window 30.

The sleeve 40 provides the further advantage that it has a lubricious nature. This feature reduces friction between the outer circumference of the cannula 11 and the patient's tissues as the cannula is advanced within and withdrawn from the patient's body. Since movement of the tissue as the cannula 11 is withdrawn can affect the proper location of the seeds 60, this reduction in friction provides a significant advantage in ensuring the accuracy of seed placement.

Figure 10:
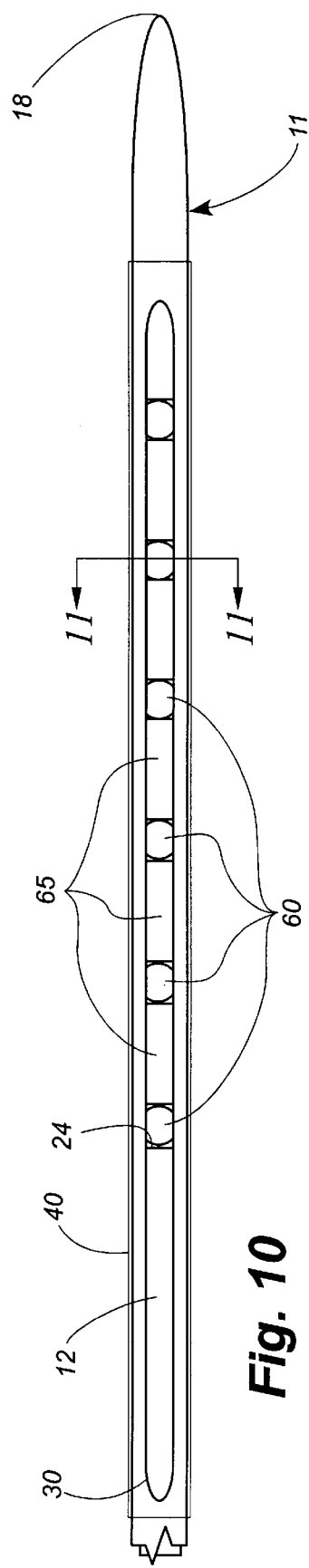
FIG. 10 is a top view of the forward portion of the hollow cannula of FIG. 2 showing radioactive seeds and intervening spacers loaded into the cannula.
Figure 11:
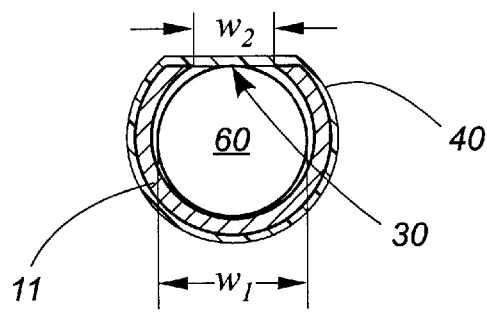
FIG. 11 is a cross-sectional view taken along line 11—11 of FIG. 10.

FIGS. 10 and 11 show the cannula 11 loaded with a plurality of radioactive brachytherapy seeds 60. The radioactive seeds 60 are of conventional design and may include, by way of example, I-125, Pd-103, or other suitable radioactive agent incorporated into a pellet or seed. Interposed between adjacent seeds 60 are spacers 65 of catgut or other bioabsorbable or biocompatible material. The spacers 65 are dimensioned to insure proper spacing between adjacent seeds 60 when the seeds are implanted within the patient's body.

FIG. 11 illustrates the relationship between the dimensions of the seeds 60 and the width of the slot 30. The seed 60 has a width $w_1$, and the slot 30 has a width $w_2$, which is less than the width $w_1$ of the seed. The seed 60 thus cannot pass through the slot 30. Further, the width of the slot 30 is sufficiently narrow that the column/hoop strength of the cannula 11 is substantially unaffected. It will thus be appreciated that the transparent sleeve 40 is not required to prevent the seeds 60 and spacers 65 from falling through the slot 30. However, the transparent covering 40 is advantageous from the perspective of preventing tissue from lapsing into the slot 30 and causing patient trauma, or possibly clogging the cannula 11 such that the seeds 60 and spacers 65 cannot properly be discharged from the forward end of the cannula needle 14.

As an alternative, rather than having a single slot 30, a plurality of shorter slots arranged longitudinally may be provided. When multiple slots are provided, a single sleeve 40 can extend over all of the slots, or individual sleeves can be provided for each slot.

The procedure for loading the radioactive seeds 60 and spacers 65 into the cannula 11 will now be explained. Prior to loading the seeds, the forward end 18 of the cannula 11 is plugged with bone wax or other suitable biocompatible (and preferably bioabsorbable) material to prevent the seeds and spacers from falling out of the forward end of the cannula 11. The plug provides the further advantage of preventing the cannula 11 from later "coring" when the cannula is introduced into the tissues of a patient. The seeds 60 and spacers 65 are then loaded into the rearward end of the cannula 11. Once the seeds 60 and spacers 65 are loaded, the stylet 12 is inserted into the rearward end 15 of the cannula 11 and advanced until the blunt forward end 24 of the stylet rod 20 confronts the rearmost seed 60. As seen in FIG. 10, the seeds 60 and spacers 65 can be viewed through the window or slot 30 in the side wall of the cannula 11. Thus the physicist loading the seeds into the cannula 11 can visually verify the proper loading sequence after the seeds 60 and spacers 65 have been loaded. Further, the physician—who was not involved in the loading process at all—can also visually verify the proper loading of the seeds 60 and spacers 65 prior to inserting the cannula into the body of the patient.

Figure 12:
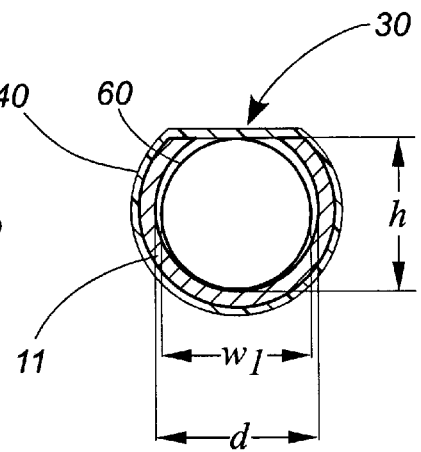
FIG. 12 is another cross-sectional view taken along line 11—11 of FIG. 10.

Referring to FIG. 12, the cannula 11 has an internal diameter d and a height h between the bottom of the cannula's lumen and the lower surface of the window 42 which is less than the cannula's internal diameter. In the cannula 11 the height h is greater than the diameter of the seeds 60 such that the seeds pass through the section of the cannula underneath the window 42 unimpeded. To prevent the seeds 60 from falling out of the forward end of the cannula 11, the forward end of the cannula is plugged with bone wax, anusol, or other suitable biocompatible agent. When the seeds 60 are deployed within the tissues of the patient, the plug is simply pushed out into the tissues along with the seeds and spacers.

By controlling the relationship between the height h at the slot 30 and the diameter of the seeds 60, it is possible to create a friction fit between the seeds and the cannula passage which will prevent the seeds from falling out of the forward end of the cannula. In the case of a seed 60 having a width $w_1$ less than the internal diameter d of the cannula 11 but at least as great as the height h, the window 42 can exert a frictional force against the seeds 60 which can help retain the seeds within the cannula 11 until affirmatively deployed by the force of the stylet 12. Under this arrangement a plug of bone wax is not necessary to prevent the seeds 60 from falling out of the forward end of the cannula 11.

Figure 13:
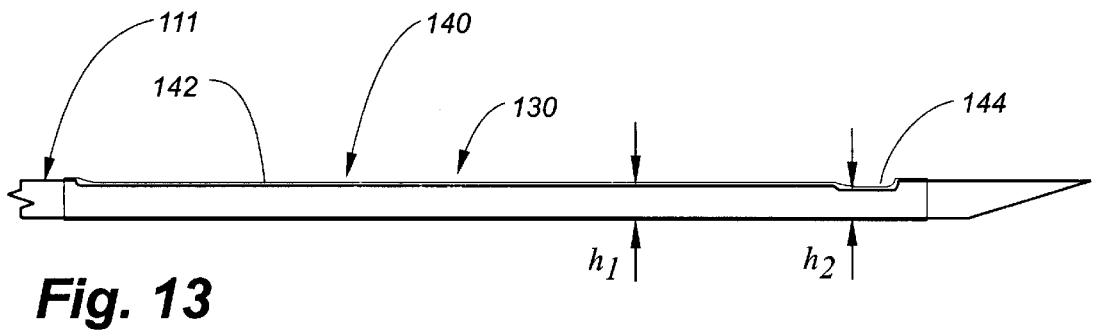
FIG. 13 is a side view of the forward end of the cannula of a first alternate embodiment of a brachytherapy seed needle with window.

However, having the internal height of the cannula reduced to a dimension smaller than the diameter of the seeds over the entire length of the window 42 can create excessive drag against the seeds and make deployment difficult. Accordingly, an alternate embodiment of a cannula 111 shown in FIG. 13 has a slot 130 which has a wider portion 144 at its forward end. A transparent sleeve 140 is disposed around the cannula 111 overlying the slot 130 to form a window 142. The window 142 is thus lower at the wider portion 144 of the slot 130. The cannula passage has a height $h_1$ over most of the length of the window 142, and a height $h_2$ at the forward portion 144 of the window which is less than the height $h_1$. The height $h_1$ is greater than the diameter of the seeds 60, while the height $h_2$ is less than the diameter of the seeds. The seeds 60 thus pass freely under the major portion of the window 142, but the forward portion 144 of the window 142 presents an obstruction which prevents the seeds 60 from falling out of the forward end of the cannula 111 under the force of gravity. However, when an axial force is exerted against the column of seeds by the stylet 12, the seeds 60 can be forced past the obstruction to be deployed within the tissues of the patient.

Figure 14:
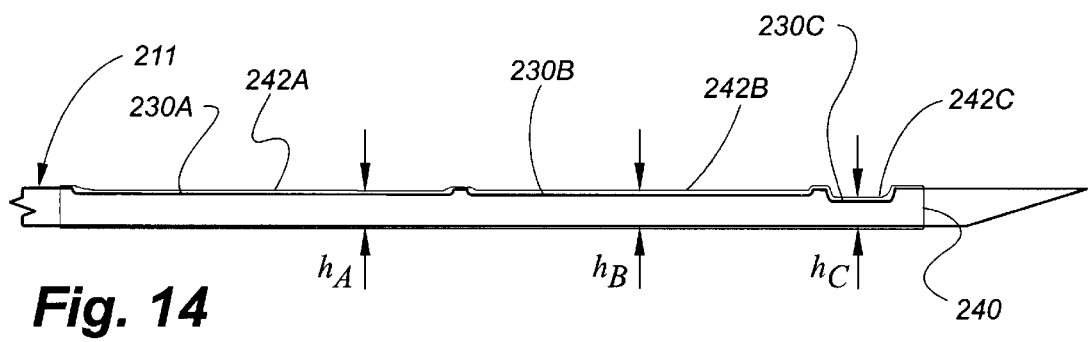
FIG. 14 is a side view of the forward end of the cannula of a second alternate embodiment of a brachytherapy seed needle with window.

Instead of providing a single slot which has portions of different width, an alternative is to provide a plurality of slots, one of which is wider than the others. Referring to FIG. 14, a cannula 211 includes a plurality of slots 230A, 230B, 230C covered by a transparent sleeve 240, with the forwardmost slot 230C being wider than the other slots. The height $h_C$ of the cannula passageway beneath the front window 242C is thus shorter than the heights $h_A$, $h_B$ beneath the other windows 242A, 242B. Further, the heights $h_A$, $h_B$ beneath the other windows 242A, 242B are greater than the diameter of the seeds 60, while the height $h_C$ of the cannula passageway beneath the front window 242C is shorter than the diameter of the seeds. The seeds 60 thus pass beneath the windows 242A, 242B unobstructed until they confront the restricted cannula height $h_C$, where they are prevented from passing until an axial force is applied against the column of seeds by the stylet 12.

It will be appreciated that other types of transparent covers may be used in place of the cylindrical sleeve 40, and that the transparent cover need not be comprised of shrink-wrap material. Further, the transparent cover need not extend completely around the circumference of the cannula 11, so long as the cover is attached in such a way that it will cover the slot 30 without becoming dislodged. Also, the cover need not be completely transparent but may be merely translucent, so long as the seeds 60 and spacers 65 within the lumen of the cannula 11 can be discerned through the cover. Finally, the cover need not be made of transparent material, so long as the cover itself is transparent. For example, a fabric woven from a material which itself is not transparent but which is loosely woven so as to permit the passage of light while being sufficiently tightly woven to prevent tissue from lapsing into the slot 30 will satisfy the requirements for the transparent cover.

The advantage of a cannula 11 sheathed in a lubricious cylindrical sleeve can be significant in comparison with a conventional metal cannula insofar as minimizing tissue displacement as the cannula is withdrawn. This advantage is so significant that a lubricious sleeve may be used on a conventional cannula which does not comprise a slot 30 or other window.

Variations in the size and configuration of the slot 30 are also possible. The length and width of the slot 30 can be varied, depending on the desired visualization of the interior of the cannula 11. The slot 30 can also be placed in any position along the length of the needle to aid in other functions of the needle. For example, the orientation of the slot 30 can provide an indication of the orientation of the bevel of the cutting forward edge of the cannula. It is also possible to form opposing slots 30 in opposite sides of the cannula 11 to prevent the physicist from having to orient the needle 10 in a particular way to visualize the interior of the cannula.

Finally, it will be understood that the preferred embodiment has been disclosed by way of example, and that other modifications may occur to those skilled in the art without departing from the scope and spirit of the appended claims.

What is claimed is:

1. A needle for implanting radioactive seeds into the body of a patient, comprising:
   a hollow cannula defining a lumen; and
   a push stylet telescopically receivable within said hollow cannula for advancing radioactive seeds through said lumen;
   said hollow cannula having a side wall and an opening formed in said side wall through which at least a portion of said lumen can be visualized.

2. The needle of claim 1, wherein said opening formed in said side wall comprises a slot formed in said side wall.

3. The needle of claim 2, wherein said slot has a width narrower than the width of the radioactive seeds that are advanced through said needle.

4. The needle of claim 2, wherein said needle further comprises a window formed by a transparent covering overlying said slot.

5. The needle of claim 2, wherein said opening comprises a plurality of longitudinal slots.

6. The needle of claim 5, wherein a single transparent covering overlies said plurality of longitudinal slots.

7. The needle of claim 5, wherein one of said plurality of longitudinal slots is wider than the others of said plurality of longitudinal slots such that when a transparent covering overlies said slots the inner diameter of said hollow cannula at said wider slot is smaller than the inner diameter of said cannula at the other of said slots.

8. The needle of claim 7, wherein said inner diameter of said hollow cannula at said wider slot is less than or equal to the diameter of a seed disposed within said cannula, whereby said transparent covering overlying said wider slot forms a portion of reduced diameter which prevents said seed from falling out of the forward end of said cannula under force of gravity.

9. The needle of claim 2, wherein said slot comprises a portion adjacent a forward end thereof which is wider than the remainder of said slot such that when a transparent covering overlies said slot the inner diameter of said hollow cannula at said wider portion is smaller than the inner diameter of said cannula at the remainder of said slot.

10. The needle of claim 9, wherein said inner diameter of said hollow cannula at said wider portion of said slot is less than or equal to the diameter of a seed disposed within said cannula, whereby said transparent covering overlying said wider portion of said slot forms a portion of reduced diameter which prevents said seed from falling out of the forward end of said cannula under force of gravity.

11. The needle of claim 4, wherein said transparent covering is comprised of a transparent material.

12. The needle of claim 4, wherein said covering comprises a sleeve of a heat-shrink material disposed about said cannula and overlying said slot.

13. The needle of claim 4, wherein said transparent covering is comprised of a lubricious material, whereby said covering prevents tissue from lapsing into said slot, permits visualization of at least a portion of the lumen of the hollow cannula, and reduces friction between said cannula and said tissues when said needle is inserted into the tissues of a patient.

14. A needle for implanting radioactive seeds into the body of a patient, comprising:

a hollow cannula having an outer periphery and defining a lumen through which radioactive seeds are delivered;

a push stylet telescopically received within said hollow cannula for advancing radioactive seeds through said lumen; and a sleeve comprised of a lubricious material and overlying at least a portion of said outer periphery of said cannula, whereby when said cannula is inserted into the tissues of a patient, said sleeve reduces friction between said cannula and said tissues.

15. The needle of claim 14, wherein said sleeve is comprised of a heat-shrinkable material.

16. The needle of claim 13, wherein said sleeve is preformed prior to being fitted around said hollow cannula.

17. A method for implanting radioactive seeds into the body of a patient, comprising the steps of:

loading into a hollow lumen of a cannula a plurality of alternating radioactive seeds and spacers, said cannula having a side wall and an opening formed in said side wall through which at least a portion of said lumen can be visualized;

subsequent to said step of loading said seeds and spacers into said cannula, visualizing at least a portion of said radioactive seeds and spacers through said opening in said side wall of said cannula to verify that said seeds and spacers are properly loaded in said cannula;

inserting a forward end of said cannula into the body of a patient to a location adjacent a target site; and ejecting said plurality of radioactive seeds and spacers into said body of said patient at said target site.

18. The method of claim 17, wherein said step of ejecting said plurality of radioactive seeds and spacers comprises the step of advancing a push stylet through said hollow lumen of said cannula to push said radioactive seeds and spacers through said lumen and out of said forward end of said cannula.

* * * * *